US012646166B2

(12) United States Patent
Mullick et al.

(10) Patent No.: US 12,646,166 B2
(45) Date of Patent: Jun. 2, 2026

(54) METHODS AND SYSTEMS FOR REDUCING QUANTITATIVE MAGNETIC RESONANCE IMAGING HETEROGENEITY FOR MACHINE LEARNING BASED CLINICAL DECISION SYSTEMS

(71) Applicant: GE Precision Healthcare LLC, Wauwatosa, WI (US)

(72) Inventors: Rakesh Mullick, Bengaluru (IN); Aanchal Mongia, Bengaluru (IN); Sudhanya Chatterjee, Bengaluru (IN); Dattesh Shanbhag, Bengaluru (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 587 days.

(21) Appl. No.: 18/182,998

(22) Filed: Mar. 13, 2023

(65) Prior Publication Data

US 2024/0312004 A1 Sep. 19, 2024

(51) Int. Cl.
| | |
|---|---|
| *G06T 7/00* | (2017.01) |
| *A61B 5/055* | (2006.01) |
| *G06T 5/70* | (2024.01) |
| *G06V 10/70* | (2022.01) |

(52) U.S. Cl.
CPC ............ *G06T 7/0012* (2013.01); *A61B 5/055* (2013.01); *G06T 5/70* (2024.01); *G06V 10/70* (2022.01); *G06T 2207/10088* (2013.01); *G06T 2207/30096* (2013.01)

(58) Field of Classification Search
CPC ......... G06T 7/0012; G06T 5/70; G06V 10/70; A61B 5/055
See application file for complete search history.

(56) References Cited

U.S. PATENT DOCUMENTS

| | | | | |
|---|---|---|---|---|
| 8,160,345 | B2 * | 4/2012 | Pavlovskaia ........... | G06V 10/46 |
| | | | | 382/131 |
| 10,755,810 | B2 * | 8/2020 | Buckler ................. | G16H 30/40 |
| 2018/0325461 | A1 * | 11/2018 | Carroll ................. | A61B 5/7267 |
| 2019/0365273 | A1 * | 12/2019 | Jara ........................ | A61B 5/055 |

(Continued)

OTHER PUBLICATIONS

Naranjo, I. et al., "Diagnostic value of diffusion-weighted imaging with synthetic b-values in breast tumors: comparison with dynamic contrast-enhanced and multiparametric MRI," European Radiology, vol. 31, No. 1, Aug. 11, 2020, 12 pages.

(Continued)

*Primary Examiner* — Mohammed H Zuberi
(74) *Attorney, Agent, or Firm* — McCoy Russell LLP

(57) ABSTRACT

Various methods and systems are provided for reducing parametric heterogeneity in quantitative magnetic resonance (qMR) images, to increase robustness of in-field machine learning model inferences. In one example, a method for reducing qMR image heterogeneity includes, receiving a first qMR image, acquired using a first value of an acquisition parameter, determining a target value of the acquisition parameter based on a training dataset of a machine learning model, generating a synthetic qMR image, wherein the synthetic qMR image simulates a qMR image acquired using the target value of the acquisition parameter, by mapping the first qMR image to the synthetic qMR image using an analytical model, and feeding the synthetic qMR image to the machine learning model.

16 Claims, 6 Drawing Sheets

(56)                    References Cited

U.S. PATENT DOCUMENTS

| | | | |
|---|---|---|---|
| 2020/0029853 A1* | 1/2020 | Forman ................. | A61B 5/055 |
| 2020/0175368 A1* | 6/2020 | Hu ........................... | G06N 3/08 |
| 2021/0018584 A1* | 1/2021 | Golay ................... | G01R 33/58 |
| 2021/0313046 A1* | 10/2021 | Xing ................. | G01R 33/5608 |
| 2022/0187405 A1* | 6/2022 | Wang ...................... | G06N 3/08 |
| 2022/0283252 A1* | 9/2022 | Weidlich ............. | G01R 33/561 |
| 2022/0326328 A1* | 10/2022 | Hwang ............. | G01R 33/5608 |
| 2023/0230233 A1* | 7/2023 | Brandenburg ......... | G16H 50/20 |
| | | | 382/128 |
| 2023/0358835 A1* | 11/2023 | Li .......................... | G06N 3/096 |
| 2024/0135502 A1* | 4/2024 | Huber ...................... | G06T 5/60 |
| 2024/0159850 A1* | 5/2024 | Ben-Eliezer .......... | G16H 30/40 |
| 2024/0183924 A1* | 6/2024 | Bilgic ................ | G01R 33/5616 |
| 2024/0230810 A1* | 7/2024 | Shih ........................ | G01R 33/50 |
| 2025/0029707 A1* | 1/2025 | Park ....................... | G16H 30/40 |
| 2025/0086788 A1* | 3/2025 | Freiman ................ | G06T 7/0012 |

OTHER PUBLICATIONS

Choi, B. et al., "Feasibility Study of Synthetic Diffusion-Weighted MRI in Patients with Breast Cancer in Comparison with Conventional Diffusion-Weighted MRI," Korean Journal of Radiology, vol. 21, No. 9, Sep. 2020, 9 pages.

* cited by examiner

IMAGE PROCESSING SYSTEM 202

PROCESSOR 204

NON-TRANSITORY MEMORY 206

NEURAL NETWORK MODULE 208

TRAINING MODULE 210

SYNTHETIC IMAGE GENERATOR 212

IMAGE DATABASE 214

DISPLAY DEVICE 234

USER INPUT DEVICE 232

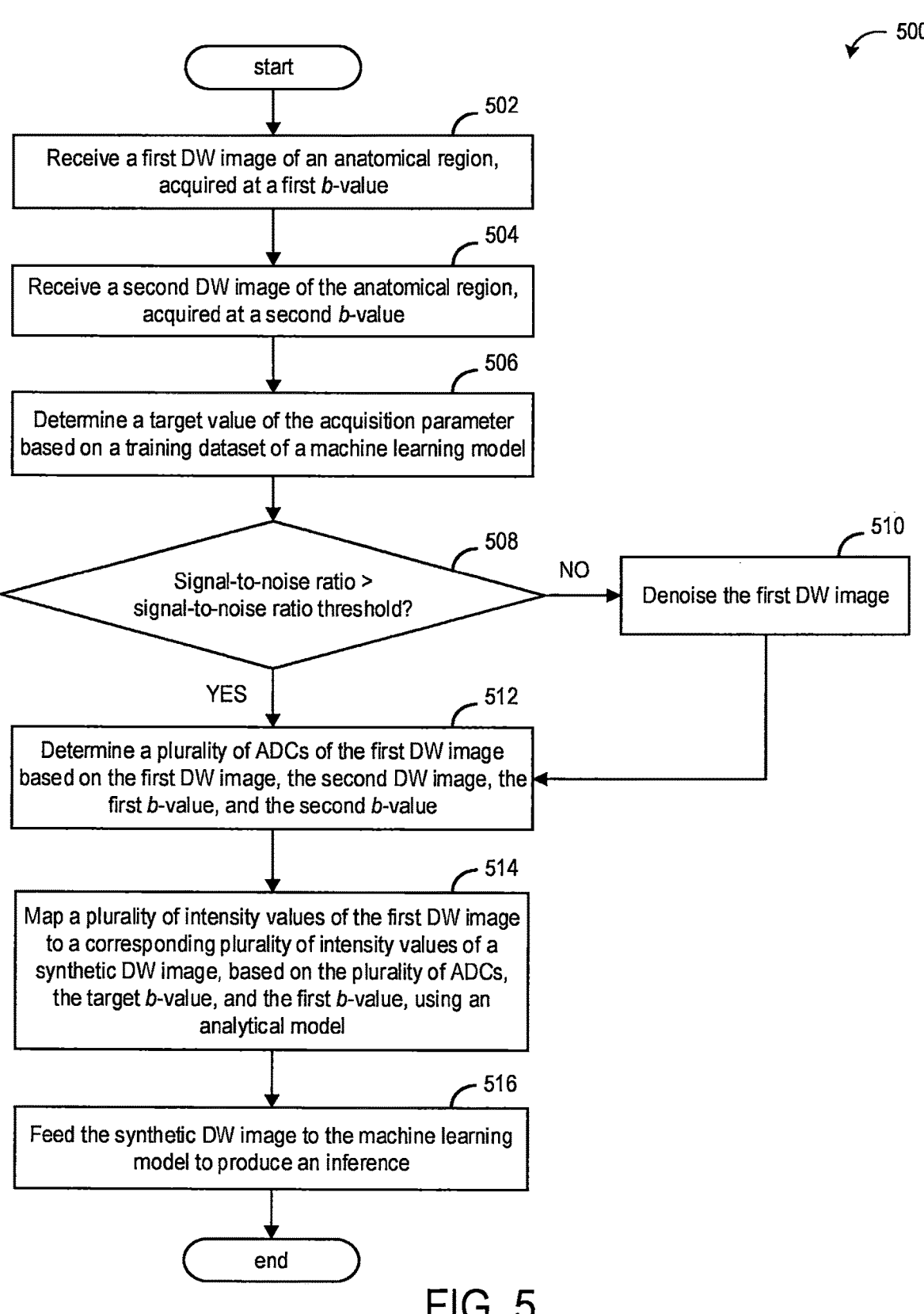

500 start

502

Receive a first DW image of an anatomical region, acquired at a first *b*-value

504

Receive a second DW image of the anatomical region, acquired at a second *b*-value

506

Determine a target value of the acquisition parameter based on a training dataset of a machine learning model

508

Signal-to-noise ratio > signal-to-noise ratio threshold?

NO

510

Denoise the first DW image

YES

512

Determine a plurality of ADCs of the first DW image based on the first DW image, the second DW image, the first *b*-value, and the second *b*-value

514

Map a plurality of intensity values of the first DW image to a corresponding plurality of intensity values of a synthetic DW image, based on the plurality of ADCs, the target *b*-value, and the first *b*-value, using an analytical model

516

Feed the synthetic DW image to the machine learning model to produce an inference end

FIG. 5

METHODS AND SYSTEMS FOR REDUCING QUANTITATIVE MAGNETIC RESONANCE IMAGING HETEROGENEITY FOR MACHINE LEARNING BASED CLINICAL DECISION SYSTEMS

FIELD

Embodiments of the subject matter disclosed herein relate to medical image processing, and more particularly, to methods and systems for reducing parameter based heterogeneity in quantitative magnetic resonance images for more consistent machine learning model training and inference.

BACKGROUND

The visual characteristics of quantitative magnetic resonance images (qMRIs) are sensitive to the acquisition parameter values used to acquire the images. For example, a diffusion weighted image (DWI) of an anatomical region may be obtained using multiple b-values (e.g., $b_1$, $b_2$, $b_3$), resulting in multiple qMRIs of the anatomical region (e.g., $DWI_1$, $DWI_2$, $DWI_3$), with distinct visual characteristics. Similarly, $T_2$ relaxometry images may be acquired for various echo times and number of echoes, resulting in observations $s_{TE_1}$, $s_{TE_2}$, ... $s_{TE_n}$, each with distinct visual characteristics/contrast. The acquisition parameter values used may vary by diagnostic center/manufacturer, making it unpredictable which acquisition parameter values may be encountered in the field. The parametric heterogeneity of qMRIs poses a challenge for machine learning (ML) based clinical decision systems (CDSs), which are trained on qMRI images to produce clinically relevant inferences. In a first example, the inferences made by the ML CDSs may be sensitive to the visual characteristics of the input qMRIs, and thus ML CDS inference confidence/consistency may be reduced when inferring based on qMRI images with visual characteristics different from those of the training dataset. In a second example, the differences in visual characteristics of qMRIs acquired using a range of acquisition parameter values may reduce an efficacy of ML model training, as the parameter value induced visual heterogeneity of the training images may occlude the salient anatomical/pathological differences correlating with prediction task (e.g., an ML model may learn a spurious correlation between a prediction task and visual differences induced by parametric heterogeneity and not underlying anatomical/pathological trends). Filtering the training data to only qMRIs acquired using a same acquisition parameter may address the issue of spurious correlations indicated above, but at the expense of a reduction in the size of the available training data. Thus, it is generally desirable to explore approaches for reducing parametric heterogeneity in qMRIs, both for training and in-field inference.

BRIEF DESCRIPTION

In one embodiment, the disclosure provides a method for reducing parametric heterogeneity induced differences in visual characteristics of qMRIs, comprising, receiving a first quantitative magnetic resonance (qMR) image, acquired using a first value of an acquisition parameter, determining a target value of the acquisition parameter based on a training dataset of a machine learning model, generating a synthetic qMR image, wherein the synthetic qMR image simulates a qMR image acquired using the target value of the acquisition parameter, by mapping the first qMR image to the synthetic qMR image using an analytical model, and feeding the synthetic qMR image to the machine learning model. The above approach enables real-time conversion of visual characteristics of a first qMR image (such as may be encountered in-field by a deployed ML CDS), to visual characteristics simulating those of the same qMR image acquired using the target value of the acquisition parameter. The target value of the acquisition parameter is determined based on the training dataset of the machine learning model (e.g., a ML CDS), thus enabling the first qMR image to be mapped to a synthetic qMR image with visual characteristics similar to those of images in the training dataset used to train the machine learning model. Further, by using an analytical model, as opposed to an ML based approach, a computational efficiency may be increased, while reducing a probability of artifact inclusion in the synthetic qMR image, such as may occur via ML model hallucination.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 5 shows a flowchart illustrating a method for reducing parametric heterogeneity in a diffusion weighted (DW) image.

DETAILED DESCRIPTION

The following description relates to various embodiments for increasing consistency and accuracy of machine learning (ML) based clinical decision system (CDS) inferences on quantitative magnetic resonance images (qMRIs), by reducing visual heterogeneity of qMRIs prior to feeding the qMRI to the ML CDS. In one aspect, the current disclosure is directed to increasing robustness of deployed ML models by aligning the visual characteristics of qMRIs encountered in-field (e.g., during deployment of the ML model at a hospital, or other imaging center), with the visual characteristics of a training dataset used to train the ML model, using an analytical model of qMRI signal formation. In one example, if a first qMR image acquired in-field is to be processed by a trained ML model, but an acquisition parameter value used to acquire the first qMR image deviates from acquisition parameter values represented in a training dataset of the trained ML model, accuracy/confidence of the inference produced by the trained ML model may be reduced. However, the current disclosure may at least partially address the above issue by generating a synthetic qMR image which simulates the first qMR image if acquired using an acquisition parameter included in the training dataset of the ML model. In other words, the synthetic qMR image may retain anatomical features captured in the first qMR image, but with visual characteristics similar to those of qMR images within the training dataset of the trained ML model.

In another aspect, the current disclosure is directed to increasing ML model training efficacy by reducing visual heterogeneity in a training dataset by mapping a plurality of qMR training images, which may have been acquired using a plurality of distinct values of an acquisition parameter, to a corresponding plurality of synthetic qMR training images. The plurality of synthetic qMR training images possess visual characteristics simulating those of the same plurality of qMR training images acquired using a target value of the acquisition parameter. In this way, an existing corpus of training data may be cast to an appearance simulating acquisition via a target value of an acquisition parameter, bypassing the need to filter out images acquired using non-target values of the acquisition parameter, and enabling more of the existing corpus of training data to be employed in the training process.

Figure 1:
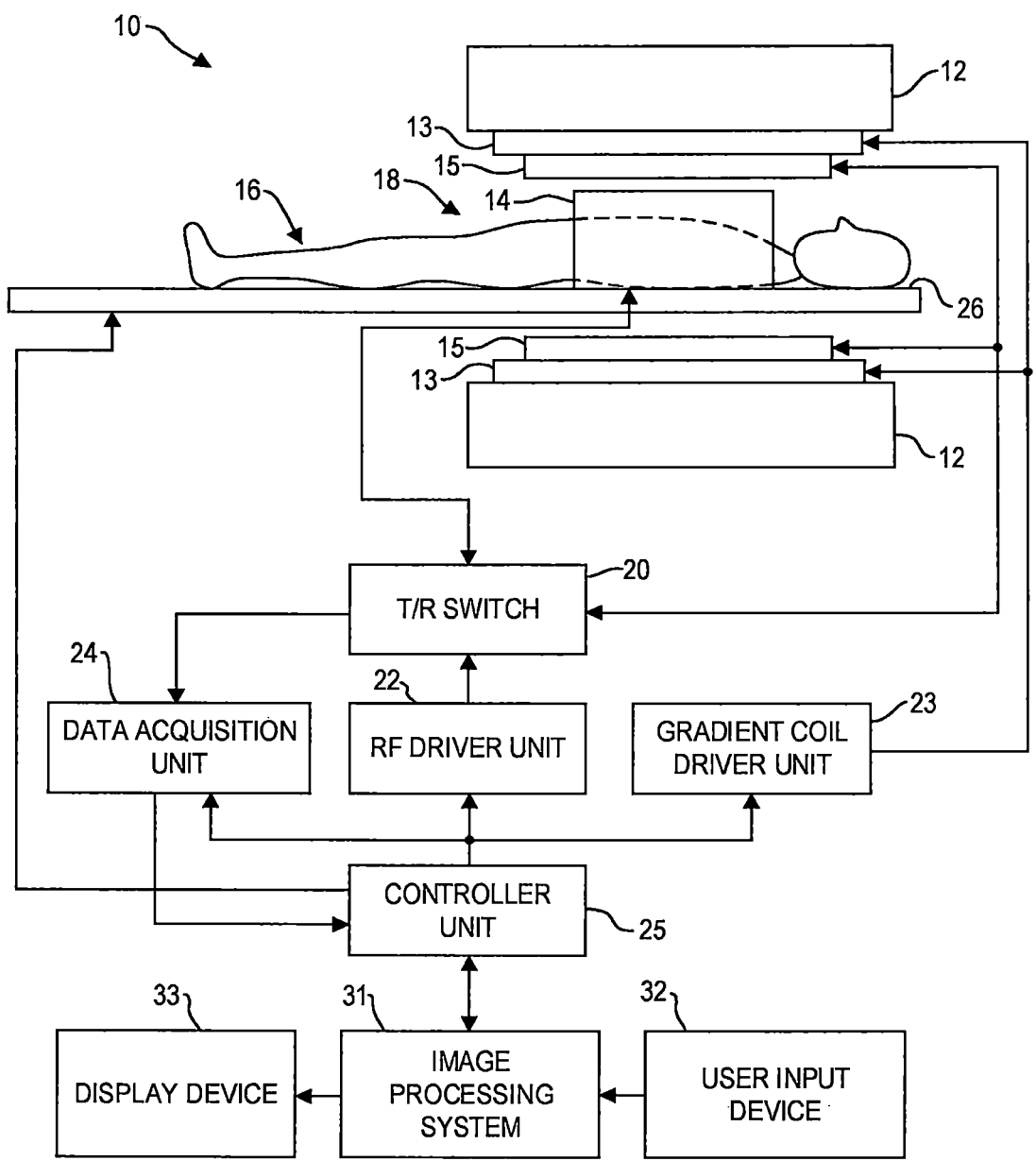
FIG. 1 illustrates a magnetic resonance imaging (MRI) system for acquiring quantitative magnetic resonance images (qMRIs), in accordance with an aspect of the disclosure.
Figure 6:
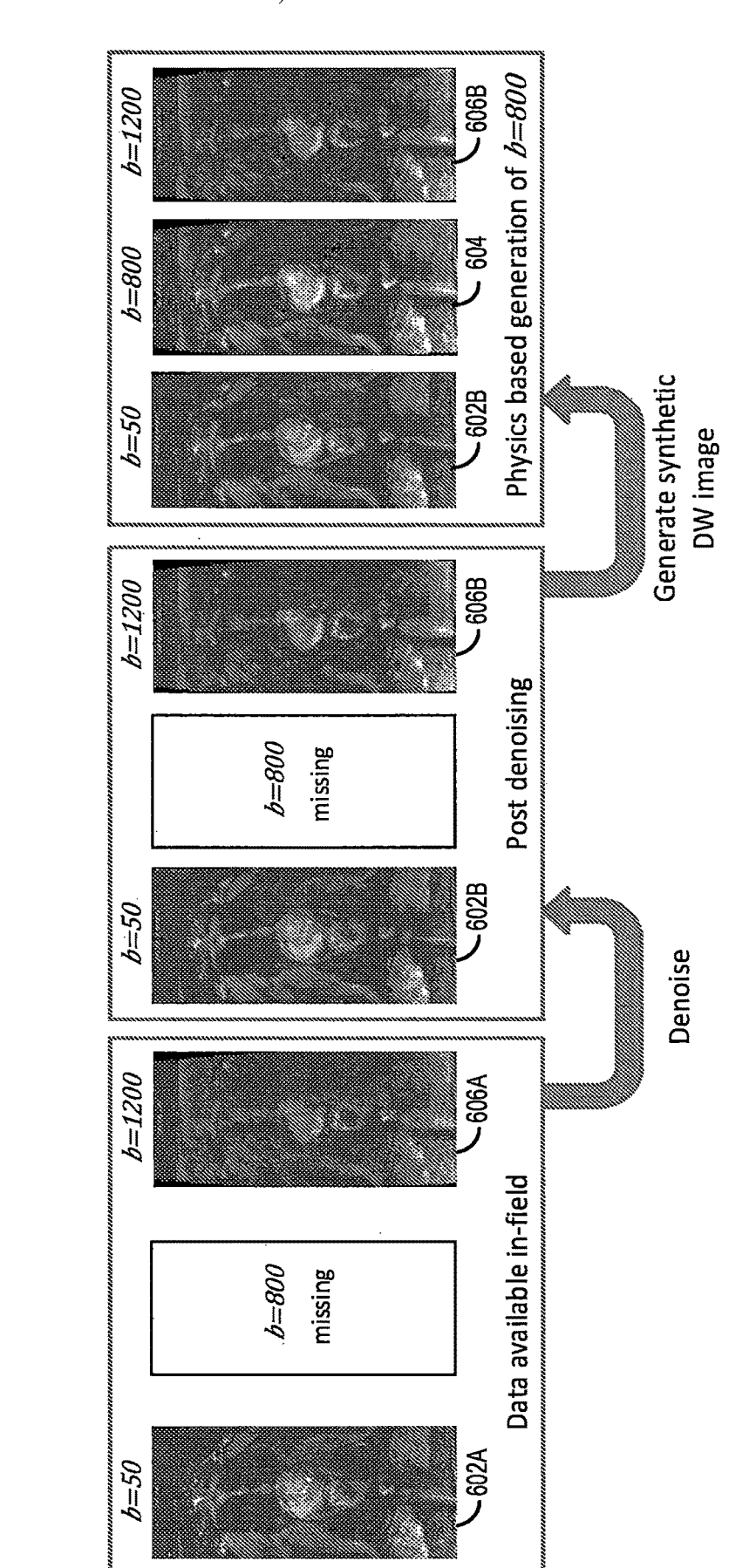
FIG. 6 shows an example process by which in-field DW images may be used to generate a synthetic DW image, according to an embodiment of the disclosure.

In various embodiments, one or more qMRIs are acquired via an MRI system, such as MRI system 10, shown in FIG. 1, using one or more values of an acquisition parameter. The acquired qMRIs may be processed by an image processing system, such as image processing system 202 shown in FIG. 2, prior to being fed to a downstream ML CDS. The image processing system may determine if the acquisition parameter value(s) used to acquire the qMRIs is/are within a threshold of a target value of the acquisition parameter, wherein the target value is determined based on a training dataset of the downstream ML CDS. If the image processing system determines that the acquisition parameter value(s) used to acquire the qMRIs deviate by greater than a threshold from the target value of the acquisition parameter, the image processing system may respond by executing one or more operations of methods 300, shown in FIG. 3, and/or 500, shown in FIG. 5, to generate synthetic versions of the qMRIs, simulating the visual characteristics of qMRIs acquired using the target value(s) of the acquisition parameter. An example process 600, illustrating how acquired qMRIs may be used to synthesize a "missing" qMRI at a target value of an acquisition parameter, is shown in FIG. 6, wherein the acquired qMRIs are diffusion weighted (DW) images. In some embodiments, the downstream ML CDS may be trained on a training dataset comprising a plurality of qMRIs, wherein the visual characteristics of the plurality of qMRIs comprising the training dataset may be normalized by executing one or more operations of method 400, shown in FIG. 4. Briefly, method 400 includes generating synthetic versions of qMRIs within the training dataset which deviate from a target value of an acquisition parameter by greater than a threshold value, to simulate a training dataset acquired at the target value of the acquisition parameter.

Referring now to FIG. 1, MRI system 10 is shown. MRI system 10 includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, an image processing system 31, a user input device 32, and a display device 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI system 10 transmits electromagnetic pulse signals to the subject 16 placed in an imaging space 18 with a static magnetic field formed to perform a scan for obtaining magnetic resonance signals from the subject 16. One or more MR images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI system 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field, $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI system 10 and replaced with another RF coil unit, the RF body coil unit 15 is fixedly attached and connected to the MRI system 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator, an RF power amplifier, and an RF oscillator that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits corresponding to the three gradient coil systems included in the gradient coil unit 13.

The data acquisition unit 24 includes a pre-amplifier, a phase detector, and an analog/digital converter used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the image processing system 31.

The MRI system 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the system to carry out operations corresponding to pre-determined scanning. The recording medium may comprise, for example, a ROM, flexible disk, hard disk, optical disk, magneto-optical disk, CD-ROM, or non-transitory memory card. The controller unit 25 is connected to the user input device 32 and processes the operation signals input to the user input device 32 and furthermore controls the table 26, RF driver unit 22, gradient coil driver unit 23, and data acquisition unit 24 by outputting control signals to them. The controller unit 25 also controls, to obtain a desired image, the image processing system 31 and the display device 33 based on operation signals received from the user input device 32.

The user input device 32 includes user input devices such as a touchscreen, keyboard, and a mouse. The user input device 32 is used by an MRI system operator, for example, to input such data as an imaging protocol, to accept or decline a scan region preview, and in some embodiments, to set a region where an imaging sequence is to be executed. The imaging protocol data, the scan region preview acceptance or declination, and the imaging sequence execution region are output to the controller unit 25.

The image processing system 31 includes a processor and non-transitory memory on which machine executable instructions may be stored, wherein the machine executable instructions may enable the processor to execute one or more of the steps of one or more of the methods herein disclosed. The image processing system 31 may be connected to the controller unit 25 and may perform data processing based on control signals received from the controller unit 25 or user input device 32. The image processing system 31 is also connected to the data acquisition unit 24 and generates spectrum data by applying various image processing operations to the magnetic resonance signals output from the data acquisition unit 24.

The display device 33 displays an image on the display screen of the display device based on control signals received from the controller unit 25. The display device 33 displays, for example, a diagnostic-scan region preview, and/or subsequent diagnostic MR images produced by the image processing system 31. Display device 33 may comprise a graphical user interface, wherein a user may interact with/input/alter one or more data fields via user input device 32. The display device 33 may display a two-dimensional (2D) slice image or three-dimensional (3D) image of the subject 16 generated by the image processing system 31.

During a scan, RF coil array interfacing cables may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils. As explained previously, the RF body coil unit 15 is a transmit coil that transmits RF signals, and the local surface RF coil unit 14 receives the MR signals. More generally, RF coils are used to transmit RF excitation signals ("transmit coil"), and to receive the MR signals emitted by an imaging subject ("receive coil"). In some embodiments, the transmit and receive coils are a single mechanical and electrical structure, or array of structures, with transmit/receive mode switchable by auxiliary circuitry. In other examples, the transmit body coil (e.g., RF body coil unit 15) and the surface receive coil (e.g., RF coil unit 14) may comprise separate components.

Figure 2:
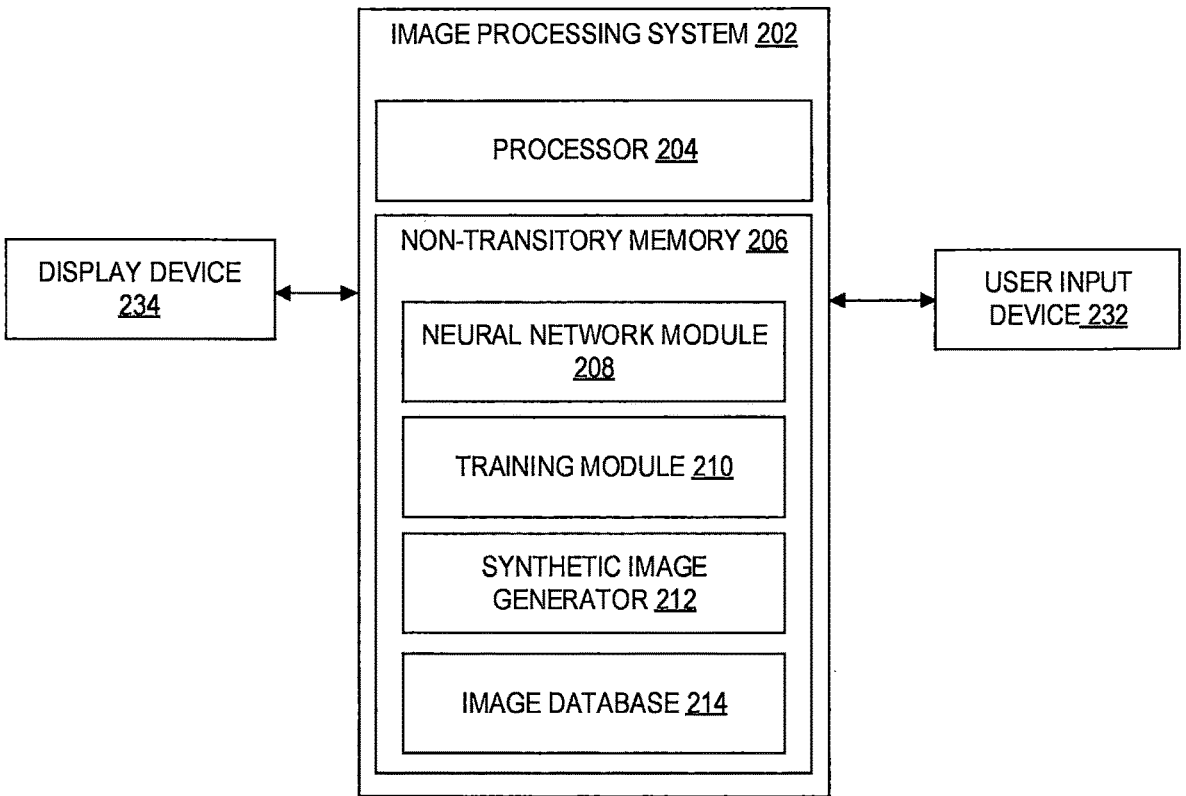
FIG. 2 illustrates an image processing system configured to generate synthetic qMRIs, using analytical models, according to an embodiment of the disclosure.

Referring to FIG. 2, image processing system 202, configured to receive and process qMRIs, is shown. In some embodiments, image processing system 202 is incorporated into the MRI system 10. For example, image processing system 202 may be provided in the MRI system 10 as image processing system 31. In some embodiments, at least a portion of image processing system 202 is disposed at a device (e.g., edge device, server, etc.) communicably coupled to the MRI system 10 via wired and/or wireless connections. In some embodiments, at least a portion of image processing system 202 is disposed at a separate device (e.g., a workstation) which can receive images from the MRI system or from a storage device which stores the images/data generated by the MRI system. Image processing system 202 may be operably/communicatively coupled to a user input device 232 and a display device 234. User input device 232 may be integrated into an MRI system, such as at user input device 32 of the MRI system 10. Similarly, display device 234 may be integrated into an MRI system, such as at display device 33 of MRI system 10.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, processor 204 may optionally include individual components that are distributed throughout two or more devices, which may be remotely located and/or configured for coordinated processing. In some embodiments, one or more aspects of processor 204 may be virtualized and executed by remotely-accessible networked computing devices configured in a cloud computing configuration.

Non-transitory memory 206 may store a neural network module 208, a training module 210, a synthetic image generator 212, and an image database 214. Neural network module 208 may include one or more ML models, which may be configured to produce inferences from qMR images, as part of a clinical decision system (CDS). In one example, the neural network module 208 may include a ML model trained to predict the presence of lesions/tumors in qMR images. Neural network module 208 may include trained and/or untrained ML models, and may further include various data, or metadata pertaining to the one or more ML models stored therein.

Non-transitory memory 206 may further store a training module 210, which may comprise instructions for training one or more of the neural networks stored in neural network module 208. Training module 210 may include instructions that, when executed by processor 204, cause image processing system 202 to conduct one or more of the steps of method 400 for reducing parametric induced visual heterogeneity in a training dataset, discussed in more detail below in reference to FIG. 4. In some embodiments, training module 210 may include instructions for implementing one or more gradient descent algorithms, applying one or more loss functions, and/or training routines, for use in adjusting parameters of one or more neural networks of neural network module 208. Training module 210 may include training datasets for the one or more neural networks of neural network module 208.

Non-transitory memory 206 also stores a synthetic image generator 212, which may include instructions for mapping qMR images acquired using a first acquisition parameter value, to synthetic images of the same qMR image (e.g., including the same anatomical regions) acquired using a target value of the acquisition parameter, using analytical models of qMRI signal formation, as described in more detail below, with reference to FIGS. 3, 5, and 6. The synthetic image generator 212 may comprise a plurality of analytical qMR signal formation models. As used herein, the term analytical model refers to a mathematical model that has a closed form solution, i.e., the solution to the equations used to describe changes in a qMRI signal as a function of acquisition parameters and/or anatomical tissue properties can be expressed as a mathematical analytic function.

Non-transitory memory 206 further stores image database 214. Image database 214 may include for example, qMRI images acquired via an MRI system, and/or synthetic qMRI images, such as may be generated by synthetic image generator 212. For example, image database 214 may store qMR images acquired via MRI system 10, and/or received from other communicatively coupled image databases. Image database 214 may further include one or more training datasets for training the one or more neural networks of neural network module 208.

In some embodiments, non-transitory memory 206 may include components disposed at two or more devices, which may be remotely located and/or configured for coordinated processing. In some embodiments, one or more aspects of non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an image to use in training a machine learning model, or for further processing using a trained machine learning model.

Display device 234 may include one or more display devices utilizing virtually any type of technology. In some embodiments, display device 234 may comprise a computer monitor, and may display MRIs, including qMRIs and synthetic qMRIs. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view MRIs produced by an MRI system, and/or interact with various data stored in non-transitory memory 206.

It should be understood that image processing system 202 shown in FIG. 2 is for illustration, not for limitation. Another appropriate image processing system may include more, fewer, or different components.

Figure 3:
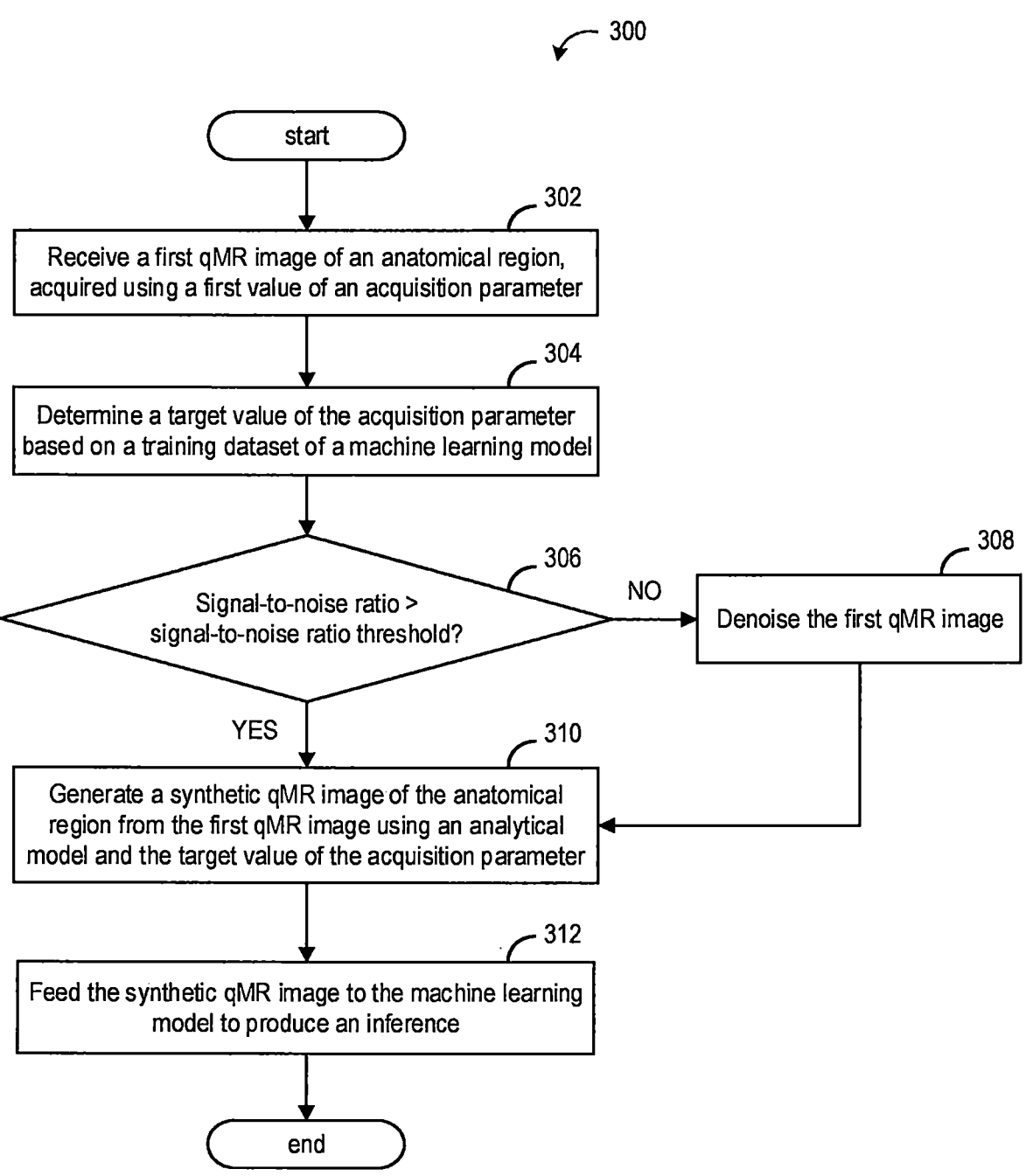
FIG. 3 shows a flowchart illustrating a high-level method for reducing parametric heterogeneity in a received qMRI, according to an embodiment of the disclosure.

Referring to FIG. 3, an exemplary method 300 for real-time reduction of parametric heterogeneity in a first qMR image, is shown. Method 300 may be executed by an image processing system, such as image processing system 202 shown in FIG. 2, prior to feeding the qMR image to a downstream, trained ML model. In some embodiments, the trained ML model may comprise an ML based CDS. The image processing system may execute one or more operations of method 300 to convert a first qMR image, acquired using a first value of an acquisition parameter, to a synthetic qMR image matching visual characteristics of qMRIs present in a training dataset of the trained ML model, thereby improving confidence/accuracy of inferences made by the trained ML model.

Method 300 begins at operation 302, wherein the image processing system receives a first qMR image of an anatomical region, acquired using a first value of an acquisition parameter. In some embodiments, the qMR image is a DW image, and the acquisition parameter is a b-value used to acquire the DW image. The b-value is a numerical value that quantifies the magnitude of the diffusion-sensitizing gradient applied during MR imaging. Generally, the higher the b-value, the more diffusion-weighted the image is, meaning that it is more sensitive to the presence of diffusion within the tissue being imaged. In some embodiments, the b-value may be set to a value of between 0 and 4000 s/mm$^2$ in order to acquire the DW image. The qMR image may also comprise a quantitative T1 image, a T2 weighted image, a proton density weighted image, a perfusion weighted image, a magnetization transfer image, or a spectroscopic image.

At operation 304, the image processing system determines a target value of the acquisition parameter based on a training dataset of a machine learning model. In some embodiments, the image processing system may retrieve the target value of the acquisition parameter from non-transitory memory, such as from metadata of the machine learning model. However, if no target value has been determined, the image processing system may dynamically determine the target value of the acquisition parameter based on the training data of the machine learning model. In some embodiments, determining the target value of the acquisition parameter based on the training dataset of the machine learning model comprises determining a most common value of the acquisition parameter used in the training dataset of the machine learning model, and setting the target value of the acquisition parameter to the most common value of the acquisition parameter used in the training dataset. In another embodiment, determining the target value of the acquisition parameter based on the training dataset of the machine learning model comprises determining an average value of the acquisition parameter used in the training dataset of the machine learning model, and setting the target value of the acquisition parameter to the average value of the acquisition parameter used in the training dataset.

At operation 306, the image processing system evaluates if a signal-to-noise ratio (SNR) of the first qMR image is greater than a signal-to-noise ratio threshold. This signal-to-noise ratio threshold may be determined based on the type of qMR imaging being used, the specific imaging parameters, the desired image quality, and other factors. If at operation 306 the image processing system determines that the SNR of the first qMR image is not greater than the signal-to-noise ratio threshold, a denoising operation may be executed at operation 308. This denoising operation can utilize a variety of techniques such as wavelet-based filtering, non-local means filtering, and total variation minimization. These techniques generally involve applying a particular algorithm which reduces unwanted noise while preserving important features of the image. After the denoising operation has been completed, method 300 may proceed to operation 310. However, if the image processing system determines that the SNR of the first qMR image is greater than the signal-to-noise ratio threshold, method 300 may proceed to operation 310, without first conducting a denoising operation.

At operation 310, the image processing system generates a synthetic qMR image of the anatomical region from the first qMR image using an analytical model and the target value of the acquisition parameter, wherein the synthetic qMR image simulates the first qMR image if acquired using the target value of the acquisition parameter. In other words, the synthetic qMR image is generated in order to simulate the first qMR image if it had been acquired using the target value of the acquisition parameter, without needing to perform an additional scan of the imaging subject. The parameters of the analytical model may include the magnetic field strength, the echo time, the flip angle, the b-value, etc.

At operation 312, the image processing system feeds the synthetic qMR image to the machine learning model to produce an inference. In some embodiments, the machine learning model is an artificial neural network, composed of an input layer, a plurality of hidden layers and an output layer. The input layer receives the synthetic qMR image and the output layer provides the inference. The hidden layers contain neurons that apply a non-linear transformation to the input data and act as a decision-making function. The weights and biases of the neurons in the hidden layer may be learned during a supervised learning process, such as backpropagation. The model then produces the inference by taking into account the synthetic qMR image, the weights and biases, and the decision-making function. By generating a synthetic qMR more closely resembling the visual characteristics of qMR images in the training dataset (acquired using the target value of the acquisition parameter), ML model inference accuracy and consistency may be improved, even when the ML model is deployed at an imaging center, hospital, etc., which uses acquisition parameters different from those present in the training dataset of the ML model. Following operation 312, method 300 may end.

Figure 4:
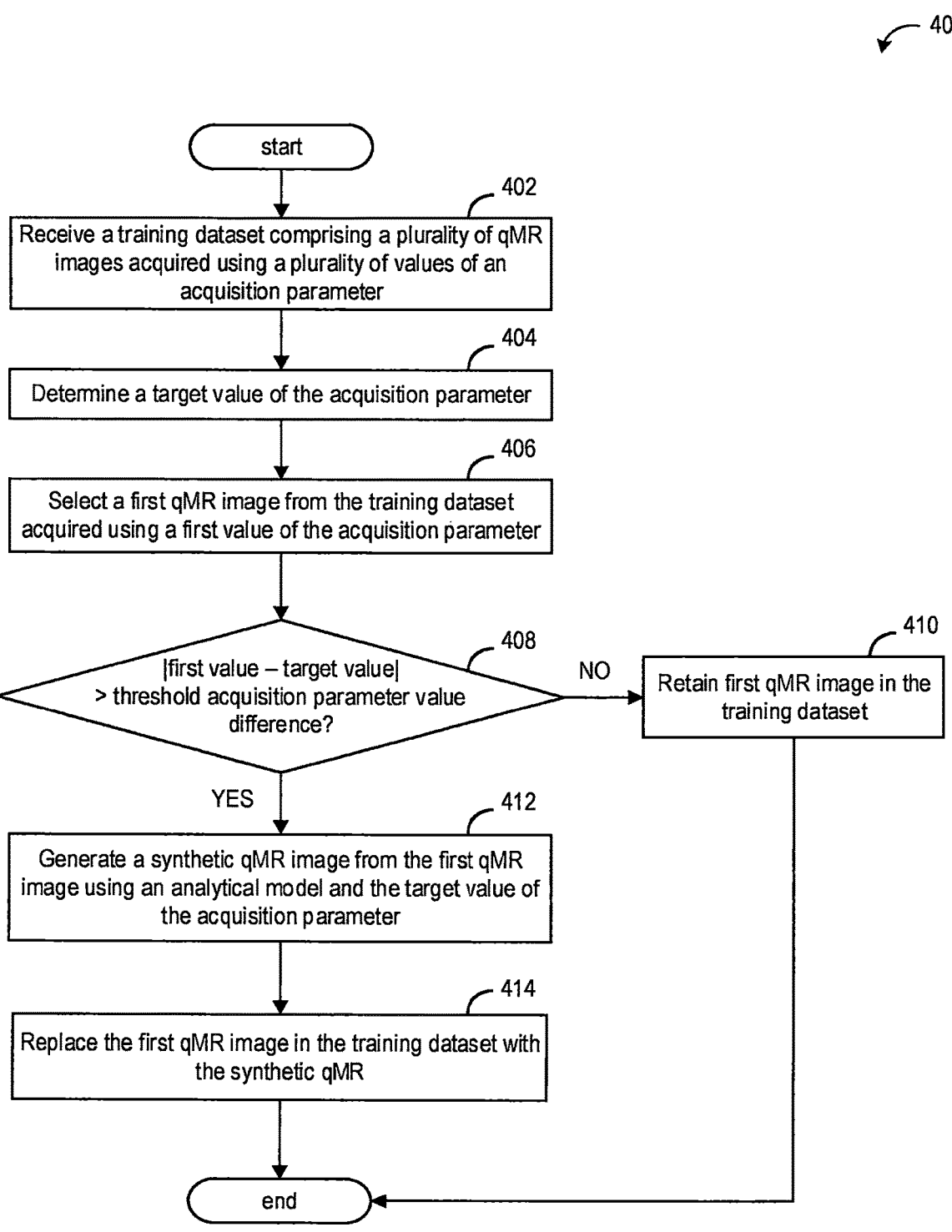
FIG. 4 shows a flowchart illustrating a high-level method for reducing parametric heterogeneity in a training dataset comprising a plurality of qMRIs, according to an embodiment of the disclosure.

Referring to FIG. 4, an exemplary method 400 for reducing parametric heterogeneity in a training dataset for a ML model, is shown. Method 400 may be executed by an image processing system, such as image processing system 202 shown in FIG. 2, prior to training the ML model. By reducing acquisition parameter based differences in visual characteristics of the images of the training dataset, the ML model may more efficiently learn correlations between anatomical features/tissue properties and inference task outcomes (e.g., detecting the presence of lesions in images, determining a volume of ischemic tissue, etc.).

Method 400 begins at operation 402, wherein the image processing system receives a training dataset comprising a plurality of qMR images acquired using a plurality of values of an acquisition parameter. In some embodiments, a training dataset may comprise a plurality of images, and ground truth labels/annotations, wherein the images may be sourced from various imaging centers or hospitals, and may be acquired by imaging systems from different manufacturers. The images of the training dataset may therefore include images acquired using a variety of distinct acquisition parameter values. Images of the training dataset may comprise qMR images including quantitative T1 images, a T2 weighted images, diffusion-weighted images, proton density weighted images, perfusion weighted images, magnetization transfer images, or spectroscopic images. In some embodiments, acquisition parameter values used to acquire the images of the training dataset may be stored in metadata of the images, such as in a DICOM header associated with each image.

At operation 404, the image processing system determines a target value of an acquisition parameter. In some embodiments, the image processing system may determine the target value of the acquisition parameter based on the training dataset. In particular, to increase a processing efficiency and to leverage the existing training data, the image processing system may determine the target value of the acquisition parameter value by determining an average, median, or mode, of values of the acquisition parameter values represented in the images of the training dataset, and may set the target value of the acquisition parameter to the average, median, or mode so determined. As an example, if a training data set comprises 1,000 DW images, 600 acquired at a b-value of 800 s/mm$^2$, 200 acquired at a b-value of 50 s/mm$^2$, and 200 acquired at a b-value of 1,200 s/mm$^2$, the image processing system may set the target value of the b-value to 800 s/mm$^2$, thereby reducing the number of synthetic images to be generated to 400.

At operation 406, the image processing system selects a first qMR image from the training dataset acquired using a first value of the acquisition parameter. In some embodiments, the image processing system may select the first qMR image from the training dataset based on the target value of the acquisition parameter determined at operation 404. For example, the image processing system may compare the target value of the acquisition parameter with the acquisition parameter values associated with the images of the training dataset, and may select the first qMR image from the training dataset whose acquisition parameter value most deviates from the target value. In some embodiments, the image processing system may select the first qMR image from the training dataset based on the signal-to-noise ratio the qMR image. For instance, the image processing system may select the qMR image from the training dataset with a highest signal-to-noise ratio. In some embodiments, the image processing system may select the first qMR image based on a pre-determined sequence. In some embodiments, the image processing system may select the first qMR image from the training dataset based on a pre-determined selection order. For example, if the target value of the acquisition parameter is set to 800 s/mm$^2$, the image processing system may select the first qMR image from the training dataset that is acquired with the closest value to 800 s/mm$^2$, such as an image acquired with a b-value of 795 s/mm$^2$. The image processing system may then select the next qMR image from the training dataset with the next closest value to 800 s/mm$^2$, such as an image acquired with a b-value of 790 s/mm$^2$. The image processing system may continue selecting qMR images from the training dataset in this manner until all qMR images are selected. In some embodiments, in addition to selecting images based on the pre-determined selection order, the image processing system may also select images from the training dataset based on additional criteria, such as image quality or image contrast.

At operation 408, the image processing system evaluates if a magnitude of the difference between the acquisition parameter value of the first qMR image and the target value is greater than a threshold acquisition parameter value difference. If at operation 408 it is determined that the magnitude of the difference between the acquisition parameter value of the first qMR image and the target value is not greater than the threshold acquisition parameter value difference, method 400 may proceed to operation 410, wherein the first qMR image is retained within the training dataset without modification, and following operation 410, method 400 may end. However, if at operation 408 the image processing system determines that the magnitude of the difference between the acquisition parameter value of the first qMR image and the target value of the acquisition parameter is greater than the threshold acquisition parameter value difference, method 400 may proceed to operation 412. In some embodiments, the threshold acquisition parameter value difference is pre-determined based on the type of image processing task for which the ML model is to be trained. For example, if the image processing task is to detect a particular tissue characteristic, the threshold acquisition parameter value difference may be set to a smaller value than if the image processing task is to detect a more general characteristic. Similarly, if the image processing task is to detect a particular tissue characteristic in a particular region, the threshold acquisition parameter value difference may be set to a lower value than if the image processing task is to detect a more general characteristic. Additionally, if the image processing task has a higher accuracy requirement, the threshold acquisition parameter value difference may be set to a smaller value than if the image processing task has a lower accuracy requirement. The threshold acquisition parameter value difference may also be adjusted based on other factors such as the noise level of the qMR images, the size of the training dataset, the particular qMR imaging system used, and the type of qMR imaging sequence used.

At operation 412, the image processing system generates a synthetic qMR image from the first qMR image using an analytical model and the target value of the acquisition parameter. A more detailed discussion of how a synthetic qMR image may be generated to simulate the visual characteristics associated with the target value of the acquisition parameter is provided in FIG. 5, below. Analytical models of qMRI signal formation generally provide a closed form equation of qMRI signal intensity as a function of acquisition parameter value(s) and one or more tissue properties. The inventors herein realized that analytical model based generation of qMR images is computationally inexpensive in comparison to ML model based methods, such as style transfer neural networks. The computational efficiency of the herein disclosed analytical model based approaches for generating synthetic qMRIs enables real-time conversion of an acquired qMR image to a desired set of visual characteristics, which is particularly advantageous in the context of real-time medical imaging and image processing. In contrast, generating synthetic MRIs using machine learning based style transfer models may require a large amount of computational power, and may not be suitable for real-time applications. Further, machine learning based style transfer models rely on training data that is representative of the target domain, which may be difficult to acquire, especially in medical imaging applications. In addition, different machine learning based style transfer models may produce different results for the same input data, due to their different architectures and training data. As a result, the variability of the generated images may be larger than desired.

At operation 414, the image processing system replaces the first qMR image in the training dataset with the synthetic qMR. Thus, the synthetic qMR image, which includes the anatomical features captured by the first qMR image but with visual characteristics associated with a target value of the acquisition parameter, may substitute for the first qMR image during training of the ML model. This enables the ML model to be trained on a training dataset with anatomical diversity similar to that of the original training dataset, but with a reduction in the parametric visual heterogeneity which often occurs in medical image datasets. In some embodiments, the target value of the acquisition parameter may be stored in non-transitory memory, along with the synthetic qMR image, such as in metadata of the synthetic qMR image. In another embodiment, the target value determined for the training dataset at operation 404 may be stored in metadata of the training dataset, as opposed to within the metadata of images within the training dataset, thereby enabling efficient access to the target value of the acquisition parameter, e.g., such as during execution of operation 304, wherein real-time determination of a target value of an acquisition parameter may be advantageous. Following operation 414, method 400 may end.

Referring to FIG. 5, an exemplary method 500 for reducing parametric heterogeneity in DW images based on a training dataset of a downstream ML model, is shown. Method 500 may be executed by an image processing system, such as image processing system 202 shown in FIG. 2, prior to feeding a DW image to a downstream, trained ML model. In some embodiments, the trained ML model may comprise an ML based CDS. The image processing system may execute one or more operations of method 500 to convert a first DW image, acquired using a first b-value, to a synthetic DW image simulating the first DW image if acquired using a target b-value, wherein the target b-value is representative of DW images in a training dataset of the trained ML model, thereby improving confidence/accuracy of inferences made by the trained ML model.

Method 500 begins at operation 502, wherein the image processing system receives a first DW image of an anatomical region, acquired using a first b-value.

At operation 504, the image processing system receives a second DW image of the anatomical region, acquired using a second b-value, wherein the first b-value and the second b-value are not equal. Both the first DW image and the second DW image may include substantially a same anatomical region, and may be acquired as part of a apparent diffusion coefficient (ADC) mapping process, wherein two or more DW images are used to determine the ADC of tissues of the anatomical region.

At operation 506, the image processing system determines a target b-value based on the training dataset of the ML model. In some embodiments, the image processing system may retrieve the target value of the acquisition parameter from non-transitory memory, such as from metadata of the ML model. However, if no target value has been determined, the image processing system may dynamically determine the target value of the acquisition parameter based on the training data of the machine learning model. In some embodiments, determining the target value of the acquisition parameter based on the training dataset of the ML model comprises determining a most common value of the acquisition parameter used in the training dataset of the ML model, and setting the target value of the acquisition parameter to the most common value of the acquisition parameter used in the training dataset. In another embodiment, determining the target value of the acquisition parameter based on the training dataset of the ML model comprises determining an average value of the acquisition parameter used in the training dataset of the ML model, and setting the target value of the acquisition parameter to the average value of the acquisition parameter used in the training dataset.

At operation 508, the image processing system evaluates if a signal-to-noise ratio (SNR) of the first DW image and the second DW image are greater than a signal-to-noise ratio threshold. In some embodiments, the SNR is determined by dividing the signal intensity of an anatomical structure by the background noise in the image. The background noise in the image may be determined by measuring the intensity of air within the DW image. In some embodiments, the SNR may be determined for each of the individual components of the image, such as the fat, water, and tissue signal.

If at operation 508 the image processing system determines that the SNR of the first DW image or the second DW image is not greater than the signal-to-noise ratio threshold, a denoising operation may be executed at operation 510. At operation 510 the image processing system may utilize a variety of techniques such as wavelet-based filtering, non-local means filtering, and total variation minimization, to increase the SNR of the first DW image and/or the second DW image. After the denoising operation has been completed, method 500 may proceed to operation 512. However, if the image processing system determines that the SNR of both the first DW image and the second DW image are greater than the signal-to-noise ratio threshold, method 500 may proceed to operation 512, without conducting a denoising operation.

At operation 512, the image processing system determines a plurality of ADCs of the first DW image based on the first DW image, the second DW image, the first b-value used to acquire the first DW image, and the second b-value used to acquire the second DW image. In some embodiments, the below equation may be used to determine the ADC for a pixel/voxel of the first DW image and the second DW image based on the DW signal intensity of the pixel/voxel in the first image ($S_{b_1}$), the DW signal intensity of the pixel/voxel in the second image ($S_{b_2}$), and first b-value used to acquire the first DW image ($b_1$), and the second b-value used to acquire the second DW image ($b_2$):

$$ADC = \frac{\ln\left(S_{b_1}/B_{b_2}\right)}{b_2 - b_1}$$

At operation 514, the image processing system maps a plurality of intensity values of the first DW image to a corresponding plurality of intensity values of a synthetic DW image, based on the plurality of ADCs determined at operation 512, the target b-value determined at operation 506, and the first b-value, using an analytical model. In some embodiments, the image processing system uses the below analytical model at operation 514 to map DW signal intensities from the first DW image to DW signal intensities of the synthetic DW image:

$$S_{b_{target}} = S_{b_1} e^{(b_1 - b_{target})ADC}$$

The above analytical model relates the DW signal intensity of a pixel/voxel of the synthetic DW image ($S_{b_{target}}$) with the DW signal intensity of a corresponding pixel/voxel from the first DW image ($S_{b_1}$), using the ADC of the corresponding pixel/voxel from the first DW image (ADC, determined at operation 514), the first b-value used to acquire the first DW image ($b_1$), and the target b-value determined at operation 506 ($b_{target}$). Each pixel/voxel of the first DW image may be associated with a distinct ADC, as the ADC is a function of the underlying tissue, and therefore the above analytical model may be used on a pixel-by-pixel or voxel-by-voxel basis to map the intensity of each pixel/voxel in the first DW image to a corresponding intensity of the pixel/voxel in the synthetic image, based on the particular ADC determined for each pixel. In some embodiments, the above analytical model may be evaluated using matrix operations.

At operation 516, the image processing system feeds the synthetic DW image to the ML model, to produce an inference. In some embodiments, the ML model is a convolutional neural network, composed of an input layer, a plurality of hidden layers (comprising one or more convolutional filters) and an output layer. The input layer receives the synthetic DW image and the output layer provides the inference. The hidden layers contain neurons that apply a non-linear transformation to the input data and act as a decision-making function. The weights and biases of the neurons in the hidden layer may be learned during a supervised learning process, such as backpropagation. The model then produces the inference by taking into account the synthetic DW image, the weights and biases, and the decision-making function. By generating a synthetic DW more closely resembling the visual characteristics of DW images in the training dataset (acquired using the target value of the acquisition parameter), ML model inference accuracy and consistency may be improved, even when the ML model is deployed at an imaging center, hospital, etc., which uses acquisition parameters different from those present in the training dataset of the ML model. Following operation 516, method 500 may end.

Referring to FIG. 6, an exemplary process 600 is shown, wherein DW image data available in-field lacks a DW image at a target b-value of 800 s/mm$^2$. The target b-value may correspond to a b-value used to generate DW images used to train a ML model, and therefore performing inferences on either of images 602A or 606A, which were acquired with b-values of 50 s/mm$^2$ and 1200 s/mm$^2$, respectively, may produce non-optimal inference performance. Instead of repeating the DW image acquisition, which may be time consuming and inconvenient for the imaging subject, the "missing" DW image at a target b-value of 800 s/mm$^2$ may be synthesized using one or more of the operations disclosed herein. In particular, exemplary process 600 includes denoising the first DW image 602A and the second DW image 606A to produce first denoised DW image 602B, and second denoised DW image 606B. The first denoised DW image 602B, and second denoised DW image 606B may be used to generate synthetic DW image 604, such as by executing using an analytical model of DW signal formation to map DW signal intensities from either the first denoised DW image 602B, and second denoised DW image 606B, as described in more detail with reference to FIG. 5, above. The synthetic DW image 604 includes the same anatomical features of first DW image 602A and second DW image 606A, but with tissue contrast similar to a DW image of the same anatomical region acquired using a b-value of 800 s/mm$^2$, or in other words, the synthetic DW image 604 simulates a DW image of the anatomical features acquired at the target b-value, bypassing the need to rescan the imaging subject.

The disclosure also provides support for a method comprising: receiving a first quantitative magnetic resonance (qMR) image, acquired using a first value of an acquisition parameter, determining a target value of the acquisition parameter based on a training dataset of a machine learning model, generating a synthetic qMR image, wherein the synthetic qMR image simulates a qMR image acquired using the target value of the acquisition parameter, by mapping the first qMR image to the synthetic qMR image using an analytical model, and feeding the synthetic qMR image to the machine learning model. In a first example of the method, determining the target value of the acquisition parameter based on the training dataset of the machine learning model comprises: determining a most common value of the acquisition parameter used in the training dataset of the machine learning model, and setting the target value of the acquisition parameter to the most common value of the acquisition parameter used in the training dataset. In a second example of the method, optionally including the first example, determining the target value of the acquisition parameter based on the training dataset of the machine learning model comprises: determining an average value of the acquisition parameter used in the training dataset of the machine learning model, and setting the target value of the acquisition parameter to the average value of the acquisition parameter used in the training dataset. In a third example of the method, optionally including one or both of the first and second examples the method further comprising: storing the target value of the acquisition parameter as metadata of the machine learning model. In a fourth example of the method, optionally including one or more or each of the first through third examples, generating the synthetic qMR image includes: determining a signal-to-noise ratio of the first qMR image, and responding to the signal-to-noise ratio of the first qMR image being below a threshold signal-to-noise ratio by: denoising the first qMR image to produce a de-noised qMR image, and mapping the de-noised qMR image to the synthetic qMR image using the analytical model. In a fifth example of the method, optionally including one or more or each of the first through fourth examples, the acquisition parameter is a b-value, the target value is a target b-value, the first qMR image is a first diffusion weighted (DW) image of an anatomical region acquired using a first b-value, wherein the first b-value is not equal to the target b-value, and wherein the synthetic qMR image is a synthetic DW image of the anatomical region. In a sixth example of the method, optionally including one or more or each of the first through fifth examples the method further comprising: receiving a second DW image of the anatomical region, acquired using a second b-value, wherein the first b-value and the second b-value are not equal, and wherein the first b-value and the second b-value are not equal to the target b-value. In a seventh example of the method, optionally including one or more or each of the first through sixth examples, generating the synthetic qMR image comprises: determining a plurality of apparent diffusion coefficients (ADCs) corresponding to a plurality of intensity values of the first DW image based on the first DW image, the second DW image, the first b-value, and the second b-value, and mapping the plurality of intensity values of the first DW image to a corresponding plurality of intensity values of the synthetic DW image using the plurality of ADCs, the target b-value, the first b-value, and the analytical model.

The disclosure also provides support for a method comprising: receiving a training dataset comprising a plurality of quantitative magnetic resonance (qMR) images acquired using a plurality of distinct values of an acquisition parameter, determining a target value of the acquisition parameter, for a first qMR image of the plurality of qMR images: determining if a value of the acquisition parameter used to acquire the first qMR image is within a threshold of the target value of the acquisition parameter, responding to the value of the acquisition parameter used to acquire the first qMR image not being within the threshold of the target value of the acquisition parameter by: generating a synthetic qMR image by mapping the first qMR image to the synthetic qMR image using an analytical model, wherein the synthetic qMR image simulates the first qMR image if acquired using the target value of the acquisition parameter, and replacing the first qMR image in the training dataset with the synthetic qMR image. In a first example of the method, determining the target value of the acquisition parameter comprises: determining a most common value of the plurality of distinct values of the acquisition parameter for the plurality of qMR images of the training dataset, and setting the target value of the acquisition parameter to the most common value of the plurality of distinct values of the acquisition parameter. In a second example of the method, optionally including the first example, determining the target value of the acquisition parameter comprises: determining an average value of the plurality of distinct values of the acquisition parameter for the plurality of qMR images of the training dataset, and setting the target value of the acquisition parameter to the average value of plurality of distinct values of the acquisition parameter. In a third example of the method, optionally including one or both of the first and second examples, generating the synthetic qMR image includes: determining a signal-to-noise ratio of the first qMR image, and responding to the signal-to-noise ratio of the first qMR image being below a threshold signal-to-noise ratio by: denoising the first qMR image to produce a de-noised qMR image, and mapping the de-noised qMR image to the synthetic qMR image using the analytical model. In a fourth example of the method, optionally including one or more or each of the first through third examples, the acquisition parameter is a b-value, the target value is a target b-value, the first qMR image is a first diffusion weighted (DW) image of an anatomical region acquired using a first b-value, wherein the first b-value is not equal to the target b-value, and wherein the synthetic qMR image is a synthetic DW image of the anatomical region. In a fifth example of the method, optionally including one or more or each of the first through fourth examples the method further comprising: selecting a second DW image of the anatomical region from the training dataset, wherein the second DW image was acquired using a second b-value, wherein the first b-value and the second b-value are not equal, and wherein the first b-value and the second b-value are not equal to the target b-value. In a sixth example of the method, optionally including one or more or each of the first through fifth examples, generating the synthetic qMR image comprises: determining a plurality of apparent diffusion coefficients (ADCs) corresponding to a plurality of intensity values of the first DW image based on the first DW image, the second DW image, the first b-value, and the second b-value, and mapping the plurality of intensity values of the first DW image to a corresponding plurality of intensity values of the synthetic DW image using the plurality of ADCs, the target b-value, the first b-value, and the analytical model. In a seventh example of the method, optionally including one or more or each of the first through sixth examples the method further comprising: responding to the value of the acquisition parameter used to acquire the first qMR image being within the threshold of the target value of the acquisition parameter by: retaining the first qMR image in the training dataset.

The disclosure also provides support for a system comprising: instructions, stored in non-transitory memory, and a processor, communicatively coupled to the non-transitory memory, that when executing the instructions causes the system to: receive a first quantitative magnetic resonance (qMR) image, acquired using a first value of an acquisition parameter, determine a target value of the acquisition parameter based on a training dataset of a machine learning model, generate a synthetic qMR image, wherein the synthetic qMR image simulates a qMR image acquired using the target value of the acquisition parameter, by mapping the first qMR image to the synthetic qMR image using an analytical model, and feed the synthetic qMR image to the machine learning model. In a first example of the system, the machine learning model is a machine learning based clinical decision system (ML CDS). In a second example of the system, optionally including the first example, the acquisition parameter is a b-value, the target value is a target b-value, the first qMR image is a first diffusion weighted (DW) image of an anatomical region acquired using a first b-value, wherein the first b-value is not equal to the target b-value, and wherein the synthetic qMR image is a synthetic DW image of the anatomical region, and wherein, when executing the instructions, the processor is further configured to cause the system to receive a second DW image of the anatomical region, acquired using a second b-value, wherein the first b-value and the second b-value are not equal, and wherein the first b-value and the second b-value are not equal to the target b-value. In a third example of the system, optionally including one or both of the first and second examples, the processor is configured to generate the synthetic qMR image by causing the system to: determine a plurality of apparent diffusion coefficients (ADCs) corresponding to a plurality of intensity values of the first DW image based on the first DW image, the second DW image, the first b-value, and the second b-value, and map the plurality of intensity values of the first DW image to a corresponding plurality of intensity values of the synthetic DW image using the plurality of ADCs, the target b-value, the first b-value, and the analytical model.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method comprising:
receiving a first quantitative magnetic resonance (qMR) image, acquired using a first value of an acquisition parameter;
determining a target value of the acquisition parameter based on a training dataset of a machine learning model via determining an average value of the acquisition parameter used in the training dataset of the machine learning model and setting the target value of the acquisition parameter to the average value of the acquisition parameter used in the training dataset;
generating a synthetic qMR image, wherein the synthetic qMR image simulates a qMR image acquired using the target value of the acquisition parameter, by mapping the first qMR image to the synthetic qMR image using an analytical model; and feeding the synthetic qMR image to the machine learning model.

2. The method of claim 1, further comprising producing an inference via the machine learning model based on the synthetic qMR image, weights and biases of neurons in a hidden layer, and a decision-making function.

3. The method of claim 1, the method further comprising:
storing the target value of the acquisition parameter as metadata of the machine learning model.

4. The method of claim 1, wherein generating the synthetic qMR image includes:
determining a signal-to-noise ratio of the first qMR image; and
responding to the signal-to-noise ratio of the first qMR image being below a threshold signal-to-noise ratio by:
denoising the first qMR image to produce a de-noised qMR image; and
mapping the de-noised qMR image to the synthetic qMR image using the analytical model.

5. The method of claim 1, wherein the acquisition parameter is a b-value, the target value is a target b-value, the first qMR image is a first diffusion weighted (DW) image of an anatomical region acquired using a first b-value, wherein the first b-value is not equal to the target b-value, and wherein the synthetic qMR image is a synthetic DW image of the anatomical region.

6. The method of claim 5, the method further comprising:
receiving a second DW image of the anatomical region, acquired using a second b-value, wherein the first b-value and the second b-value are not equal, and wherein the first b-value and the second b-value are not equal to the target b-value.

7. The method of claim 6, wherein generating the synthetic qMR image comprises:
determining a plurality of apparent diffusion coefficients (ADCs) corresponding to a plurality of intensity values of the first DW image based on the first DW image, the second DW image, the first b-value, and the second b-value; and
mapping the plurality of intensity values of the first DW image to a corresponding plurality of intensity values of the synthetic DW image using the plurality of ADCs, the target b-value, the first b-value, and the analytical model.

8. A method comprising:
receiving a training dataset comprising a plurality of quantitative magnetic resonance (qMR) images acquired using a plurality of distinct values of an acquisition parameter;
determining a target value of the acquisition parameter, wherein determining the target value comprises determining a most common value of the plurality of distinct values of the acquisition parameter for the plurality of qMR images of the training dataset and setting the target value of the acquisition parameter to the most common value of plurality of distinct values of the acquisition parameter;
for a first qMR image of the plurality of qMR images:
determining if a value of the acquisition parameter used to acquire the first qMR image is within a threshold of the target value of the acquisition parameter;
responding to the value of the acquisition parameter used to acquire the first qMR image not being within the threshold of the target value of the acquisition parameter by:
generating a synthetic qMR image by mapping the first qMR image to the synthetic qMR image using an analytical model, wherein the synthetic qMR image simulates the first qMR image if acquired using the target value of the acquisition parameter; and
replacing the first qMR image in the training dataset with the synthetic qMR image.

9. The method of claim 8, wherein the synthetic qMR image comprises anatomical features captured by the first qMR image and visual characteristics associated with the target value of the acquisition parameter.

10. The method of claim 8, wherein generating the synthetic qMR image includes:
determining a signal-to-noise ratio of the first qMR image; and
responding to the signal-to-noise ratio of the first qMR image being below a threshold signal-to-noise ratio by:
denoising the first qMR image to produce a de-noised qMR image; and
mapping the de-noised qMR image to the synthetic qMR image using the analytical model.

11. The method of claim 8, wherein the acquisition parameter is a b-value, the target value is a target b-value, the first qMR image is a first diffusion weighted (DW) image of an anatomical region acquired using a first b-value, wherein the first b-value is not equal to the target b-value, and wherein the synthetic qMR image is a synthetic DW image of the anatomical region.

12. The method of claim 11, the method further comprising:
selecting a second DW image of the anatomical region from the training dataset, wherein the second DW image was acquired using a second b-value, wherein the first b-value and the second b-value are not equal, and wherein the first b-value and the second b-value are not equal to the target b-value.

13. The method of claim 12, wherein generating the synthetic qMR image comprises:
determining a plurality of apparent diffusion coefficients (ADCs) corresponding to a plurality of intensity values of the first DW image based on the first DW image, the second DW image, the first b-value, and the second b-value; and
mapping the plurality of intensity values of the first DW image to a corresponding plurality of intensity values of the synthetic DW image using the plurality of ADCs, the target b-value, the first b-value, and the analytical model.

14. The method of claim 8, the method further comprising:
responding to the value of the acquisition parameter used to acquire the first qMR image being within the threshold of the target value of the acquisition parameter by:
retaining the first qMR image in the training dataset.

15. A system comprising:
instructions, stored in non-transitory memory; and
a processor, communicatively coupled to the non-transitory memory, that when executing the instructions causes the system to:
receive a first quantitative magnetic resonance (qMR) image, acquired using a first value of an acquisition parameter;
determine a target value of the acquisition parameter based on a training dataset of a machine learning model;
generate a synthetic qMR image, wherein the synthetic qMR image simulates a qMR image acquired using the target value of the acquisition parameter, by mapping the first qMR image to the synthetic qMR image using an analytical model; and feed the synthetic qMR image to the machine learning model; wherein the acquisition parameter is a b-value, the target value is a target b-value, the first qMR image is a first diffusion weighted (DW) image of an anatomical region acquired using a first b-value, wherein the first b-value is not equal to the target b-value, and wherein the synthetic qMR image is a synthetic DW image of the anatomical region; and wherein, when executing the instructions, the processor is further configured to cause the system to receive a second DW image of the anatomical region, acquired using a second b-value, wherein the first b-value and the second b-value are not equal, and wherein the first b-value and the second b-value are not equal to the target b-value;

the processor is configured to generate the synthetic qMR image by causing the system to:

determine a plurality of apparent diffusion coefficients (ADCs) corresponding to a plurality of intensity values of the first DW image based on the first DW image, the second DW image, the first b-value, and the second b-value; and map the plurality of intensity values of the first DW image to a corresponding plurality of intensity values of the synthetic DW image using the plurality of ADCs, the target b-value, the first b-value, and the analytical model.

16. The system of claim 15, wherein the machine learning model is a machine learning based clinical decision system (ML CDS).

* * * * *